(12) United States Patent
Hogt et al.

(10) Patent No.: US 6,566,391 B2
(45) Date of Patent: May 20, 2003

(54) TRIOXEPAN COMPOUNDS

(75) Inventors: Andreas H. Hogt, AB Enschede (NL); John Meijer, ES Deventer (NL); Rene Gerritsen, TA Loosdrecht (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/930,400

(22) Filed: Aug. 15, 2001

(65) Prior Publication Data

US 2002/0040152 A1 Apr. 4, 2002

Related U.S. Application Data

(60) Provisional application No. 60/225,316, filed on Aug. 15, 2000.

(30) Foreign Application Priority Data

Nov. 10, 2000 (EP) .............................................. 00203943

(51) Int. Cl.⁷ ..................... A61K 31/335; C07D 323/00
(52) U.S. Cl. ........................................ 514/450; 549/352
(58) Field of Search ........................... 549/352; 514/450

(56) References Cited

U.S. PATENT DOCUMENTS 5,856,412 A  * 1/1999  Bock et al. .................. 525/387

FOREIGN PATENT DOCUMENTS

| EP | 355 733 | 2/1990 | ......... C07C/409/40 |
|---|---|---|---|
| WO | WO 96/03397 | 2/1996 | ......... C07D/323/00 |
| WO | WO 98/50354 | 11/1998 | ......... C07C/409/00 |

OTHER PUBLICATIONS

Kirk Othmer's Encyclopedia of Chemical Technology, "Peroxides and Peroxy Compounds, Organic", 3$^{rd}$ Ed, vol. 17, pp. 27 and 57 (1982).

* cited by examiner

*Primary Examiner*—Alan L. Rotman
*Assistant Examiner*—Raymond Covington
(74) *Attorney, Agent, or Firm*—Richard P. Fennelly

(57) ABSTRACT

The invention relates to compounds of formulae I and II (I)

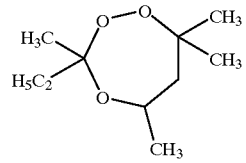

(II)

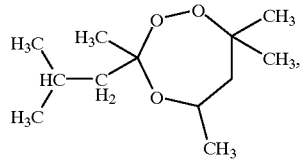

and compositions comprising these compounds.

3 Claims, No Drawings

TRIOXEPAN COMPOUNDS

This application claims the benefit of Provisional application Ser. No. 60/225,316, filed Aug. 15, 2000.

The present invention relates to two new trioxepan compounds, or substituted 1,2,4-trioxacycloheptanes.

Organic peroxides have long been known for a variety of uses. One such known compound, see for instance Kirk & Othmer's *Encyclopedia of Chem. Tech.*, 3$^{rd}$ Ed, Vol.17, page 57, is a 1,2,4-trioxacycloheptane of formula (X)

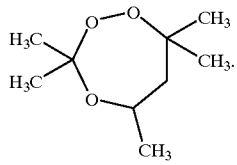

(X)

WO 98/50354 discloses the use of this compound, as well as that of four related trioxepan compounds, including the product of formula (Y) together with a co-agent in cross-linking processes.

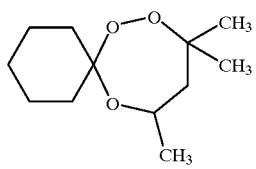

(Y)

The compounds disclosed thus far were found not to be efficient enough and/or cost-efficient enough when used in, for instance, controlled degradation processes of polypropylene and/or high-solid acrylate polymerization processes. Probably for these reasons the trioxepan compounds are not commonly used in industry. Rather, typically use is made of other types of organic peroxides, even though such peroxides need to be phlegmatized (diluted) in order to allow safe handling and/or are costly.

Surprisingly, we have found two new 1,2,4-trioxacycloheptanes with improved properties that can be used as alternatives to the peroxides conventionally used in these processes, such as 2,5-di-tert.butylperoxy-2,5-dimethyl hexane and 3,6,9-triethyl-3,6,9-trimethyl-1,4,7-triperoxononane.

Accordingly, the present invention relates to these two new 1,2,4-trioxacycloheptane compounds. More particularly, we claim the two compounds of formulae I and II

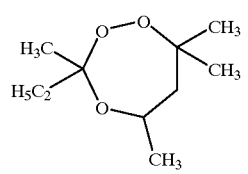

(I)

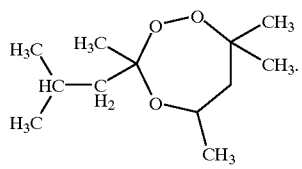

(II)

The compounds could be synthesized in a conventional way by reacting HOC(CH$_3$)HCH$_2$C(CH$_3$)$_2$OOH with methyl ethyl ketone and methyl iso-butyl ketone, respectively. If so desired, they can be phlegmatized using suitable conventional phlegmatizing agents.

As said above, it was found that these compounds were particularly useful for degrading polypropylene and making polyacrylates for use in high-solid coating compositions, as is detailed in the examples below.

Experimental

Chemicals used:

Borealis® HC001A-B1 homo-polypropylene powder (PP) ex Borealis
Irganox® 1010 ex Ciba Specialty Chemicals
Trigonox® 101 (2,5-di-tert.butylperoxy-2,5-dimethyl hexane) ex Akzo Nobel
Trigonox® 301 3,6,9-triethyl-3,6,9-trimethyl-1,4,7-triperoxononane ex Akzo Nobel
Solvesso® 100 and Exxate® 700 ex ExxonMobil All other chemicals used were supplied by Acros Chemicals, analytical quality, and used without further purification.

EXAMPLES 1–5 AND COMPARATIVE EXAMPLES A–H

In these examples peroxides (when used) were dissolved in dichloromethane (approx. 5% by weight solution) and mixed with the PP in an amount such that 0.005% or 0.01% by weight of active oxygen was introduced (based on the weight of the polypropylene, see table below). Also 0.1% by weight, based on the weight of the PP, of Irganox® 1010 stabilizer was mixed in. The mixtures were placed in a cupboard overnight at room temperature to remove the dichloromethane. The resulting mixture was fed into a Haake Rheocord® system 40 with Rheomex® TW 100 intensive mixing screws using a Plasticolor 2000 single screw pump with screwhousing type 15/22. In order to maintain low oxygen conditions, nitrogen was introduced into the hopper (2.5 l/minute) and around the die (9 l/minute) of the Rheocord.

During extrusion the screw speed was set to 50 rpm and the temperature settings were 190/250/250/250° C. (condition 1) or 160/225/225/225° C. (condition 2).

The resulting strand was cooled using a water bath and granulated using an Automatik® ASG5 granulator. Before analysis, the granules were dried overnight at 60° C.

The MFI of the polymer was analyzed in the conventional way using method ASTM D 1238 (230° C./2.16 kg).

The following results were achieved:

| Example | Peroxide | Act. O in PP | Extruder condition | Torque (Nm) | MFI (g/10 min) |
|---|---|---|---|---|---|
| 1 | Formula I | 0.005% | 1 | 16 | 82 |
| 2 | Formula I | 0.010% | 1 | 13 | 215 |
| 3 | Formula I | 0.010% | 2 | 25 | 292 |
| 4 | Formula II | 0.005% | 2 | 29 | 112 |
| 5 | Formula II | 0.010% | 2 | 25 | 265 |
| A | None | 0 | 1 | 24 | 3 |
| B | None | 0 | 2 | 23 | 3 |
| C | Formula X | 0.010% | 2 | 26 | 228 |
| D | Formula Y | 0.010% | 1 | 32 | 14 |
| E | Trigonox ® 101 | 0.005% | 1 | 34 | 30 |
| F | Trigonox ® 101 | 0.010% | 2 | 32 | 71 |
| G | Trigonox ® 301 | 0.010% | 1 | 18 | 84 |
| H | Trigonox ® 301 | 0.010% | 2 | 28 | 84 |

This shows that compounds of formulae I and II are very efficient in the controlled gradation of PP, especially for making PP with a high MFI. The inefficiency of product X may be partly related to its volatility.

EXAMPLES 6 TO 8 and COMPARATIVE EXAMPLES I AND J

In these examples acrylates are polymerized in a solvent using a jacketed glass reactor with a diameter of 60 mm and a height of 80 mm, equipped with a turbine stirrer, a reflux condenser, and an injection port.

Solvent (40 g) was added to the reactor. The temperature was adjusted such that the peroxide used in the experiment has a half life of 15 minutes at said temperature. For polymerization temperatures up to and including 126° C., butyl acetate was used as the solvent. For polymerizations from 126 up to and including 165° C. Solvesso® 100 was used, while Exxate® 700 was used for polymerizations at a temperature from 165–200° C.

Nitrogen was used to obtain oxygen-free polymerization conditions.

Monomers (40 g butyl acrylate, 28 g hydroxyethyl methacrylate, 20 g styrene, 10 g methyl methacrylate, and 2 g methacrylic acid) and 30 meq. (30 mmoles for a compound with one OO bond per molecule, 15 mmoles for a compound with two OO bonds per molecule, etc.) initiator were metered into the reactor using a Watson Marlow pump over a 4-hour period. Thereafter the polymerization was continued for another hour at the same temperature.

The resulting polymer was analyzed in a conventional way. The molecular weights were determined by HP-SEC, using polystyrene standards. The solids content (solids) of the resin that was produced was determined by gravimetric analysis by accurately weighing about 1 g of resin, dissolving this sample in about 10 g of toluene, and subsequently drying it in an oven with forced air circulation for 4 hours at 125° C. After cooling of the sample, the weight of the residual material divided by the weight of the original sample is the solids content. The viscosity was measured using a Brookfield viscometer at 25° C.

The reference product "cyclic-MIAKP" was produced on-site using the procedure as given for composition V in WO 96/03397, but using iso-amyl ketone instead of isobutyl ketone. The product was phlegmatized and contained 67.3% by weight of peroxide. As another reference Trigonox® 301 (cyclic-MEK peroxide, 41% solution in an odourless mineral spirit) ex Akzo Nobel was used. These compounds are considered to be representative of modern high-solid acrylate polymerization initiators. The trioxepans according to the invention were in the technically pure form and contained more than 95% by weight of peroxide. The results are presented below.

| Example | Peroxide | Polymerization temperature | Solids (%) | Mw | Mn | D |
|---|---|---|---|---|---|---|
| 6 | Formula I | 180 | 69.9 | 4,500 | 1,750 | 2.5 |
| 7 | Formula I | 200 | 70.0 | 2,400 | 1,300 | 1.8 |
| 8 | Formula II | 165 | 69.2 | 5,700 | 2,750 | 2.0 |
| I | cyclic-MIAKP | 180 | 70.8 | 6,000 | 1,900 | 3.1 |
| J | Trigonox ® 301 | 200 | 71.3 | 2,900 | 1,500 | 2.0 |

These results show that the trioxepans according to the invention are very efficient initiators for making low-molecular weight high-solid acrylate resins that have a narrow molecular weight distribution.

We claim:

1. A compound of the formula:

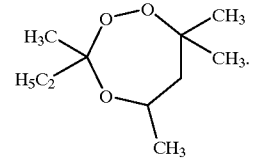

2. A compound of the formula:

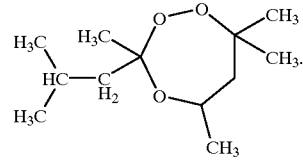

3. A composition comprising at least a compound of either claim 1 or claim 2 and a phlegmatizing agent.

* * * * *